United States Patent
Abraham et al.

(10) Patent No.: US 10,031,087 B2
(45) Date of Patent: Jul. 24, 2018

(54) METHODS AND SYSTEMS FOR THE QUANTITATIVE MEASUREMENT OF INTERNAL DEFECTS IN AS-CAST STEEL PRODUCTS

(71) Applicant: SSAB Enterprises, LLC, Lisle, IL (US)

(72) Inventors: Sunday O. Abraham, Bettendorf, IA (US); Yufeng Wang, Bettendorf, IA (US); Justin P Raines, Davenport, IA (US); Richard L. Bodnar, Bettendorf, IA (US); Jason E Thomas, Daphne, AL (US); Steven S. Hansen, Batavia, IL (US)

(73) Assignee: SSAB Enterprises, LLC, Lisle, IL (US)

( * ) Notice: Subject to any disclaimer, the term of this patent is extended or adjusted under 35 U.S.C. 154(b) by 0 days.

(21) Appl. No.: 15/273,206

(22) Filed: Sep. 22, 2016

(65) Prior Publication Data

US 2018/0080881 A1    Mar. 22, 2018

(51) Int. Cl.
*G06K 9/00* (2006.01)
*G01N 21/88* (2006.01)
(Continued)

(52) U.S. Cl.
CPC ......... *G01N 21/8851* (2013.01); *G01N 21/95* (2013.01); *G06T 7/0004* (2013.01);
(Continued)

(58) Field of Classification Search
None
See application file for complete search history.

(56) References Cited

U.S. PATENT DOCUMENTS

| 4,331,872 A | 5/1982 | Soga et al. |
| 4,519,041 A | 5/1985 | Fant et al. |

(Continued)

FOREIGN PATENT DOCUMENTS

| CN | 101819150 A | 9/2010 |
| CN | 101949851 A | 1/2011 |

OTHER PUBLICATIONS

International Search Report and Written Opinion on Internationl Appl. No. PCT/US17/52791, dated Oct. 19, 2017, 7 pgs.

(Continued)

*Primary Examiner* — Atiba O Fitzpatrick
(74) *Attorney, Agent, or Firm* — Greenberg Traurig, LLP

(57) ABSTRACT

A method for quantitatively measuring internal defects in an as-cast steel product includes optically scanning at least a portion of a surface of the steel product with a scanning device to create a digital image thereof. The method further includes thresholding the image in a thresholding engine to isolate internal defects within the image and analyzing the thresholded image to determine an internal defect area, wherein the internal defect area includes an area of at least a portion of the thresholded image that is occupied by the internal defects. The method further includes determining an overall area of the portion of the thresholded image, calculating a fraction of the internal defect area relative to the overall area, and calculating an equivalent Mannesmann scale rating of the internal defects in the steel product based on the fraction.

63 Claims, 12 Drawing Sheets

(51) Int. Cl.
G06T 7/00 (2017.01)
G01N 21/95 (2006.01)
(52) U.S. Cl.
CPC .............. G01N 2021/8887 (2013.01); G06T 2207/30164 (2013.01)

(56) References Cited

U.S. PATENT DOCUMENTS

| | | | |
|---|---|---|---|
| 4,809,765 | A | 3/1989 | Ueshima et al. |
| 4,875,371 | A | 10/1989 | Gronsfeld et al. |
| 5,083,867 | A | 1/1992 | Burk |
| 5,509,460 | A | 4/1996 | Chun et al. |
| 5,537,206 | A | 7/1996 | Akiyoshi et al. |
| 2002/0116980 | A1 | 8/2002 | Kerr et al. |
| 2006/0204108 | A1 | 9/2006 | Littooij et al. |
| 2009/0126492 | A1 | 5/2009 | Sato |
| 2010/0103256 | A1 | 4/2010 | Rauber |
| 2012/0074095 | A1 | 3/2012 | Yoo et al. |
| 2015/0098655 | A1* | 4/2015 | Chang ............... G06K 9/00543 382/192 |
| 2015/0302568 | A1* | 10/2015 | Hirai ................. G01N 23/2254 382/149 |
| 2016/0203593 | A1 | 7/2016 | Henkemeyer et al. |

OTHER PUBLICATIONS

J.K. Brimacombe; "Empowerment with Knowledge — toward the Intelligent Mold for the Continuous Casting of Steel Billet," Metallurgical Transactions B, vol. 24B, 1993, pp. 917-335.
I.V. Samarasekera; "Ingenuity and Innovation — The Hallmarks of Brimacombe's Pioneering Contributions to Process Engineering," Metallurgical and Materials Transactions B, vol. 33B, 2002, pp. 5-29.
"Classification of Defects in Materials—Standard Charts and Sample Guide," SN960, SMS Demag, Feb. 2009.
"Pipeline and Hazardous Materials Safety Administration: Standards for Increasing the Maximum Allowable Operating Pressure for Gas Transmission Pipelines," 49 CFR Part 192, Part V, Department of Transportation, Oct. 17, 2008.
Sunday Abraham, Josh Cottrell, Justin Raines, Yufeng Wang, Rick Bodnar, Samuel Wilder, Jason Thomas and Jerry Peters; "Development of an Image Analysis Technique for Quantitative Evaluation of Centerline Segregation in As-cast Products," AISTech 2016, vol. II, pp. 1585-1598.
L. J. Radziemski and D.A. Cremers, Handbook of Laser-induced Breakdown Spectroscopy, New York: John Wiley. ISBN 0-470-09299-8. , 2006, pp. 1,302.
A.W. Miziolek, V. Palleschi and I. Schechter, "Laser-induced Breakdown Spectroscopy (LIBS): Fundamentals and Applications." Cambridge, UK, Cambridge University Press, 2006, pp. 498-513.
F. Boué-Bigne, "Laser-induced Breakdown Spectroscopy Applications in the Steel Industry: Rapid Analysis of Segregation and Decarburization," Spectrochimica Acta, 2008, pp. 1122-1129.
I. Taguchi and H. Hamada, "Development of New Computer-Aided Microanalyzer and its Application to Iron and Steel Analysis," Analytical Sciences, vol. 1, 1985, pp. 119-124.
K. Miyamura, S. Kitamura, S. Sakaguchi, C. Hamaguchi and M. Hirai, "Development of Segregation Etch Print Method Its Application to Investigation of CC Slab Segregation," ISIJ International, vol. 24, 1984, pp. 718-725.
"Slab Centerline Carbon Analysis for Calibration of University of Iowa Segregation Model", SSAB Americas R&D, unpublished research, 2013.

A. Gosh, "Segregation in Cast Products," Sadhana, vol. 26, Parts 1&2, 2001, pp. 5-24.
M.J. Gray, C.C. Chen and S.V. Subramanian, "Centerline Segregation for Plate and Strip Produced from Continuously Cast Slabs," AGA-NG-18 Contract PR-187-9212, 1996.
S.K. Choudhary and S. Ganguly, "Morphology and Segregation in Continuously Cast High Carbon Steel Billets," ISIJ International, vol. 47, No. 12, 2007, pp. 1759-1766.
M.O. El-Bealy, "Macrosegregation Quality Criteria and Mechanical Soft Reduction for Central Quality Problems in Continuous Casting of Steel," Materials Sciences and Applications, 5, 2014, pp. 724-744.
M.O. El-Bealy, "New Segregation Criteria for Quality Problems in Continuous Casting of Steel," Ironmaking &Steelmaking, vol. 40, 8, pp. 559-570.
C. Daly, D. Jeulin, D. Benoit and G. Auclair, "Application of Multivariate Geo-statistics to Microprobe Mappings in Steels,"ISIJ International, vol. 30, No. 7, 1990, pp. 529-534.
J. Sengupta, J. Casey, D. Crosbie, B.D. Nelson, G. Kladnik and N. Gao, "Qualitative and Quantitative Techniques for Evaluating Manganese Segregation in Advanced High-Strength Steels at ArcelorMittal Dofasco's No. 1 Continuous Caster," AISTech 2011 Proceedings, pp. 731-740.
H.F. Jacobi, "Investigation of Centerline Segregation and Centerline Porosity in CC-Slabs," Steel Research, vol. 74, No. 11/12, 2003, pp. 667-678.
C. Geerkens, Dr. J. Wans, D. Lieftucht, A. Krasilnikov and M. Klein, "Special Technologies and New Developments to Improve Slab Quality," AISTech 2015 Proceedings, pp. 2465-2472.
P. Kotas, P. Praks, L. Valek, V. Zeljkovic and V. Vondrak, "Automated Region of Interest Retrieval of Metallographic Images for Quality Classification in Industry," Advances in Electrical and Electronic Engineering, 2012, pp. 50-56.
L. Válek, P. PetriŠkova, P. Praks, P. Kotas and P. Jagla, "The Quality Results of Slabs at Segregation Area," Metal 2011.
H. Preßlinger, S. Ilie, P. Reisinger, A. Schiefenmüller, A. Pissenberger, E. Parteder and C. Bernard, "Methods for Assessment of Slab Center Segregation as a Tool to Control Slab Continuous Casting with Soft Reduction," ISIJ International, vol. 46, No. 12, 2006, pp. 1845-1851.
J. Komenda and G. Runnsjö, "Quantification of Macrosegregation in Continuously Cast Steel Structures," Steel Research 69, No. 6, 1998, pp. 228-236.
A. Kazakov, D. Kiselev and O. Pakhomova, "Microstructural Quantification for Pipeline Steel Structure-Property Relationships," CIS Iron and Steel Review, 2012, pp. 4-12.
O. Haida, H. Kitaoka, Y. Habu, S. Kakihara, H. Bada and S. Shiraishi, "Macro- and Semi-macroscopic Features of the Centerline Segregation in CC Slabs and Their Effect on Product Quality, "Transactions ISIJ, vol. 24, 1984, pp. 891-898.
J. A. Sirgo, R. Campo, A. López, A. Diaz and L. Sancho, "Measurement of Centerline Segregation in Steel Slabs," IEEE, 2006, pp. 516-520.
B. Barber, A.W.A. Smith, J. Komenda, H. Huemer, I. Luzzo, M.R. Ridolfi, P.E. Di Nunzio, V. Colla, M. Vannucci, L. Sancho, A. Diaz, J. Laine and H. Kytonen, "Prediction of Rolled Product Properties by Correlation with As-cast Structure and Rolled Product/Plant Process Variables, Including Segregation Modeling," European Commission, EUR 23309, 2008. pp. 91-92.
Masafumi Miyazaki, Tekemasa Murao and Kohichi Isobe, Formation Mechanism and Modeling of Centerline Nippon Steel Technical Report, No. 104, Aug. 2013, 48-53, 6 pgs.

* cited by examiner

METHODS AND SYSTEMS FOR THE QUANTITATIVE MEASUREMENT OF INTERNAL DEFECTS IN AS-CAST STEEL PRODUCTS

BACKGROUND

Continuous casting is the process whereby liquid steel is solidified into a "semifinished" billet, bloom, beam blank or slab for subsequent processing in a steel hot rolling mill. A billet has a square or round cross section with a typical area of about 23,226 mm², a slab has an even larger rectangular cross section; a beam blank is a near-net shape product used to feed medium and heavy section mills; and a bloom has a rectangular or round cross section with a cross sectional area larger than a billet, but smaller than that of a slab. FIG. 1 is a schematic diagram of an example slab continuous casting process 100. Once the steel has been refined in ladle 102 to achieve the desired chemical composition and temperature, ladle 102 is transported to the caster for casting. During casting, the steel flows from the bottom of ladle 102 through ladle shroud 103 into a holding bath called a tundish 104. Tundish 104 allows a reservoir of steel to continuously feed mold 108 as one ladle 102 is emptied and a new one is opened. With this arrangement, several ladles 102 of liquid steel of the same grade or closely-related grades can be continuously cast before the caster is turned around to continuously cast another sequence of heats. One ladle of steel is referred to as one heat and several ladles of steel of the same grade or closely-related grades cast continuously in this manner is referred to as a sequence of heats.

The initial solidification of a slab cast in this manner begins in mold 108, a rectangular box that may be made of copper or copper-based alloy. Water jackets may be mounted on the four sides of the mold to facilitate solidification. Mold 108 may be only about 800-900 mm long, and at its bottom, the thickness of the solidified steel 118 (referred to as the shell) may be a few millimeters thick depending on the nature of cooling in the mold. The partially solidified product 116 (referred to as the strand) is essentially like a water tank with outer solid shell and liquid interior. Strand 116 is continuously withdrawn into the secondary cooling chamber of the caster, which comprises sets of supporting water-cooled rolls 114 arranged in segments. Water spray nozzles 112 are arranged in between the rolls 114 to gradually continue and complete the solidification of the strand 116. Once solidification is complete, strand 116 is cut to length (e.g., by a torch) at cutoff point 120 and may be one of a billet, a bloom, a beam blank or a slab 200. By the time strand 116 is completely solidified, it may have traveled several tens of meters from the location of mold 108. Hence, the caster is typically designed as a curved machine to allow for space and to facilitate a better roll support system. The curved strand 116 is straightened in the horizontal portion of the machine before it is cut to length. The steel undergoes different thermal states and phase changes and experiences different degrees of mechanical stresses before casting is complete. As a result of all of these processes, the semifinished product may exhibit certain surface and internal defects due to thermal and mechanical stresses. A defect is an imperfection or a flaw in as-cast products that could deteriorate the performance of the products and render them unsuitable for their intended applications.

FIG. 2 shows examples of various types of defects commonly found in an as-cast steel product 200. Such defects include midway 201, triple-point 202, centerline 203, diagonal 204, straightening/bending 205, pinch roll surface cracks 206, mid-face longitudinal 207, corner longitudinal 208, mid-face transverse 209, corner transverse 210 and star 211 defects. The severity of these defects varies depending on casting-specific conditions. By visually inspecting the as-cast product, potential locations in the machine where these defects originate may be examined and adjusted before subsequent casting sequences. However, such diagnoses may be inadequate, due in significant part to the industry's lack of a quantitative method of evaluating the defects.

Historically, the rating of the severity of internal slab defects has been conducted by a manual, subjective and visual comparison of etched cross sections of as-cast products to the Mannesmann charts, which were developed in the 1970s. FIG. 3 shows examples of the Mannesmann charts for various centerline segregations, varying sequentially by degree. As shown, the Mannesmann charts provide a scale of five ratings denoted by the integers 1 to 5, corresponding to increasing degrees of segregation. Similar charts also exist for other types of defects, such as longitudinal (radial) internal cracks, transverse (halfway) internal cracks, narrow side internal cracks, corner internal cracks, cloud-shaped inclusions and spot-shaped inclusions. (See FIGS. 10 to 15.) Thus, when an operator is evaluating a product for the extent of, for example, centerline segregation, the operator will visually inspect the product and assign it a value between 1 and 5 based on the operator's subjective opinion of which image on the Mannesmann chart the product most closely resembles. Sometimes if the extent of segregation falls squarely between two of the Mannesmann images, the operator will assign a half-integer value, such as 2.5, to the product.

Studies show that this technique is flawed due to the inconsistent, subjective interpretations of the charts by different operators. For example, in 2008, the Pipeline and Hazardous Material Safety Administration (PHMSA) concluded that the application of Mannesmann charts for rating centerline segregation is highly subjective. By way of example, FIGS. 4A and 4B show the results of two separate sets of round-robin testing conducted by two operators. As shown, the ratings selected by the two operators varied greatly—at times by as much as a full point (i.e., a 25% difference) on the Mannesmann scale. Specifically, the correlation coefficient for the first set of round-robin testing in FIG. 4A was only 0.32, and the correlation coefficient for the second round of testing in FIG. 4B was only 0.47. Hence, the lack of reproducible results from the visual and highly subjective assessment of internal defects makes process and product developments ineffective. Further, because operators typically rate products on either a whole number or, at most, a half-whole number basis, the granularity of the Mannesmann rating scale is relatively low.

SUMMARY

This summary is provided to introduce a selection of concepts in a simplified form that are further described below in the Detailed Description set forth hereinbelow. This summary is not intended to identify key features or essential features of the claimed subject matter, nor is it intended to be used to limit the scope of the claimed subject matter.

Various embodiments of the present invention are directed to a method for quantitatively measuring internal defects, such as segregation, in an as-cast steel product. The method includes optically scanning at least a portion of a surface of the steel product with a scanning device to create a digital image thereof. The method further includes thresholding the image in a thresholding engine to isolate internal defects within the image and analyzing the thresholded image to determine an internal defect area, wherein the internal defect area includes an area of at least a portion of the thresholded image that is occupied by the internal defects. The method further includes determining an overall area of the portion of the thresholded image, calculating a fraction of the internal defect area relative to the overall area, and calculating an equivalent Mannesmann scale rating of the internal defects in the steel product, based on the fraction.

Various other embodiments are directed to a system for quantitatively measuring internal defects in an as-cast steel product. The system includes an optical scanner adapted to scan at least a portion of a surface of the steel product to create a digital image thereof. The system also includes a threshold engine communicatively coupled with the optical scanner and adapted to threshold the image to isolate internal defects within the image. The system also includes an internal defect area engine communicatively coupled with the threshold engine. The internal defect area engine is adapted to receive the thresholded image from the threshold engine and to analyze the thresholded image to determine an internal defect area. The internal defect area includes an area of at least a portion of the thresholded image that is occupied by the internal defects. The internal defect area engine is also adapted to determine an overall area of the portion of the thresholded image and to calculate a fraction of the internal defect area relative to the overall area. The system also includes a normalizer communicatively coupled with the internal defect area engine. The normalizer is adapted to receive the fraction of the internal defect area relative to the overall area from the internal defect area engine and to calculate an equivalent Mannesmann scale rating of the internal defects in the steel product, based on the fraction.

Various other embodiments are directed to a method for quantitatively measuring internal defects in an as-cast steel product. The method includes etching a surface of the steel product with an etchant selected from the group consisting of a hydrochloric acid etchant. The method also includes optically scanning at least a portion of the surface of the steel product with a scanning device to create a digital image thereof. The method further includes thresholding the image in a thresholding engine to isolate internal defects within the image and analyzing the thresholded image to determine an internal defect area, wherein the internal defect area includes an area occupied by internal defects within a portion of the thresholded image that corresponds to an equi-axed region of the surface in the case of centerline segregation; regions between the centerline and the top or bottom surface of the as-cast product in case of mid-way (radial) cracks, mid-way (transverse) cracks, cloud-shape inclusions and spot-shaped inclusions; and between the triple point and the edge (e.g. the shorter edge) of the surface of the as-cast product in the case of narrow side cracks and corner cracks. The method further includes calculating a hypothetical area of an equi-axed region of the surface from the thresholded image, calculating a fraction of the internal defect area relative to the hypothetical area of an equi-axed region, determining where the fraction falls on a curve representing the relationship between the Mannesmann scale and internal defect area fraction, and calculating an equivalent Mannesmann scale rating of the internal defects in the steel product, based on where the fraction falls on the curve.

BRIEF DESCRIPTION OF THE DRAWINGS

The accompanying drawings, which are incorporated in and form a part of this specification, illustrate embodiments of the invention and, together with the description, serve to explain the principles of embodiments of the invention.

DETAILED DESCRIPTION

Figure 1:
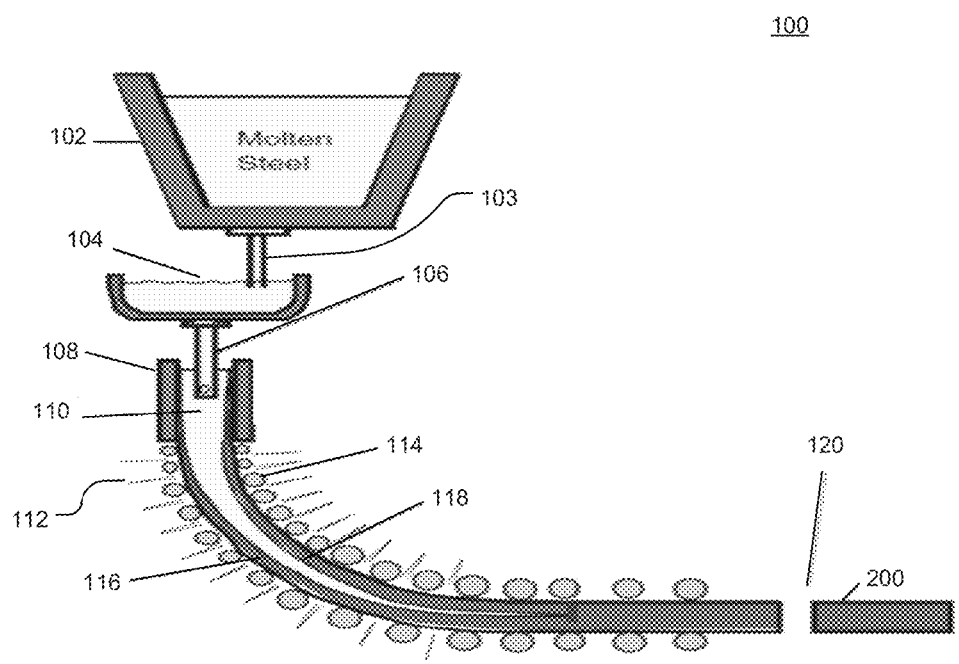
FIG. 1 is a schematic representation of a continuous casting process.

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. To the contrary, the present invention is intended to cover all alternatives, modifications and equivalents, which may be included within the spirit and scope of the invention as defined by the claims. Furthermore, in the detailed description of the present invention, numerous specific details are set forth in order to provide a thorough understanding of the present invention. However, it will be obvious to one of ordinary skill in the art that the present invention may be practiced without these specific details. In other instances, well known methods, procedures and components have not been described in detail as not to unnecessarily obscure aspects of the present invention.

Some portions of the detailed descriptions that follow may be presented in terms of procedures, processing, and other symbolic representations, some of which may involve operations on data bits within a computer or digital system memory. These descriptions and representations are some of the means used by those skilled in the data processing arts to most effectively convey the substance of their work to others skilled in the art. A procedure, process, etc., is herein, and generally, conceived to be a self-consistent sequence of steps or instructions leading to a desired result. The steps are those requiring physical manipulations of physical quantities. Sometimes, though not necessarily, these physical manipulations may take the form of electrical or magnetic signals capable of being stored, transferred, combined, compared, and otherwise manipulated in a computer system or similar electronic computing device. For reasons of convenience, and with reference to common usage, these signals are referred to as values, elements, symbols, characters, terms, numbers, or the like with reference to the present invention.

It should be borne in mind, however, that all of these terms are to be interpreted as referencing physical manipulations and quantities and are merely convenient labels that are to be interpreted further in view of terms commonly used in the art. Unless specifically stated otherwise as apparent from the discussion herein, it is understood that throughout discussions of any given embodiment, discussions utilizing terms such as "determining" or "outputting" or "transmitting" or "recording" or "locating" or "storing" or "displaying" or "receiving" or "recognizing" or "utilizing" or "generating" or "providing" or "accessing" or "checking" or "notifying" or "delivering" or the like, may at times refer to the action and processes of a computer system, or similar electronic computing device, that manipulates and transforms data. The data are represented as physical (electronic) quantities within the computer system's registers and memories and is transformed into other data similarly represented as physical quantities within the computer system memories or registers or other such information storage, transmission, or display devices.

Generally speaking, various embodiments provide automated and objective systems and processes for quantifying internal defects, including but not limited to segregation, in as-cast steel products in a highly granular manner. At a very high level, this is accomplished by first defining a reference curve of the Mannesmann scale ratings versus the fractional area of the product surface that is occupied by internal defects. Once that curve is defined, the surface of a steel product can be scanned and analyzed to determine its fractional internal defect area, and the product may then be assigned a corresponding rating on the Mannesmann scale based upon where on the curve the measured fractional internal defect area falls.

Figure 5:
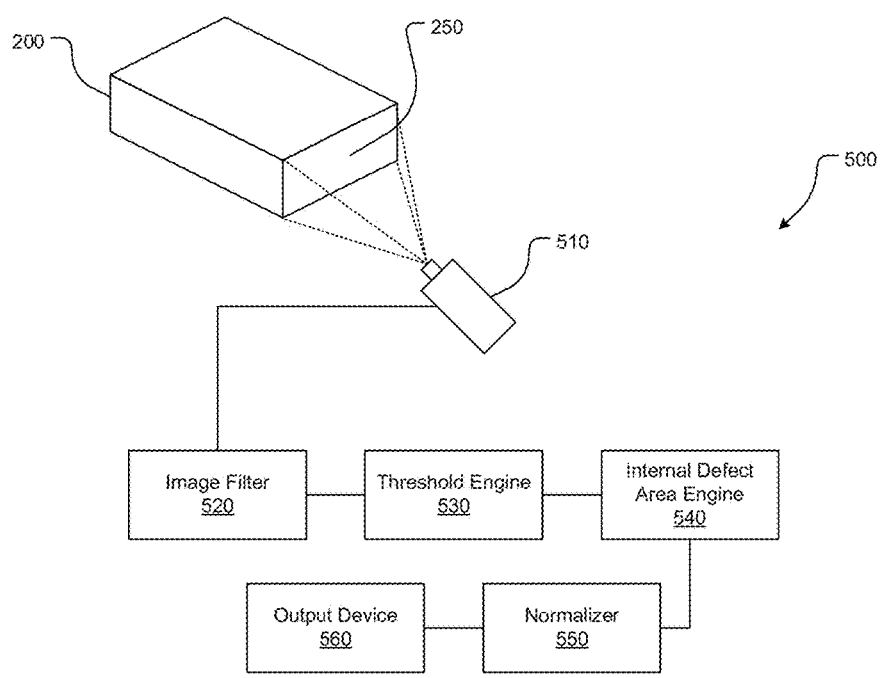
FIG. 5 is a schematic illustration showing a system for quantitatively measuring internal defects in an as-cast steel product, in accordance with various embodiments of the present invention.

FIG. 5 illustrates system 500 for quantitatively measuring internal defects in an as-cast steel product, such as a slab, billet, bloom or beam blank, in accordance with various embodiments of the present invention. System 500 includes optical scanner 510. Optical scanner 510 may be a portable scanner, a flatbed scanner, a non-contact scanner, a camera or the like. System 500 may also include image filter 520 communicatively coupled with optical scanner 510, threshold engine 530 communicatively coupled with image filter 520, internal defect area engine 540 communicatively coupled with threshold engine 530, normalizer 550 communicatively coupled with internal defect area engine 540, and output device 560 communicatively coupled with normalizer 550. The process for quantitatively measuring internal defects in an as-cast steel product will be described with reference to system 500 hereinbelow.

Figure 3:
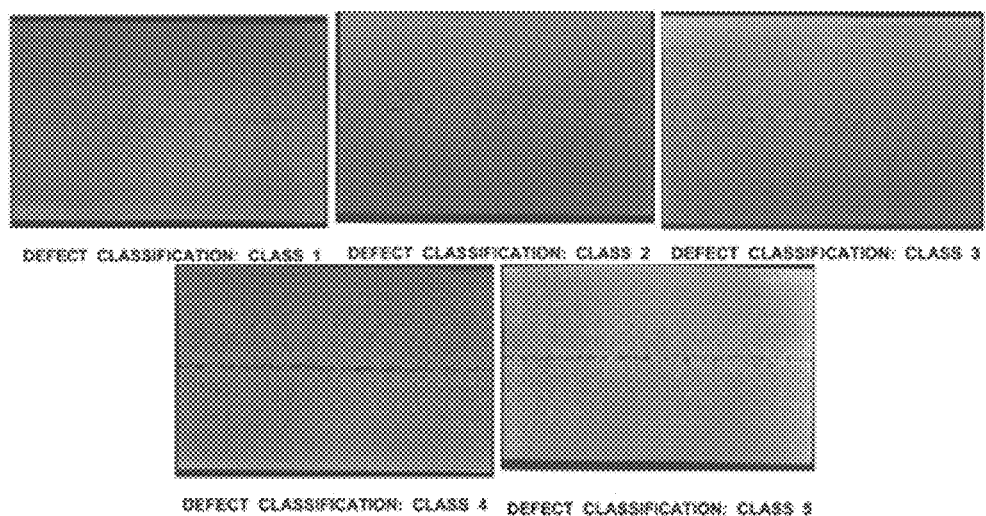
FIG. 3 is a series of photographs describing an example of the Mannesmann charts for centerline segregation.
Figure 4A:
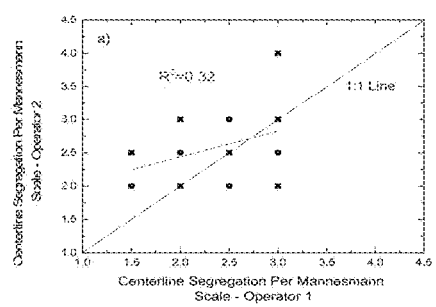
FIG. 4A is a first graph showing the results of a first set of round robin testing conducted by two operators, using conventional Mannesmann rating techniques.
Figure 4B:
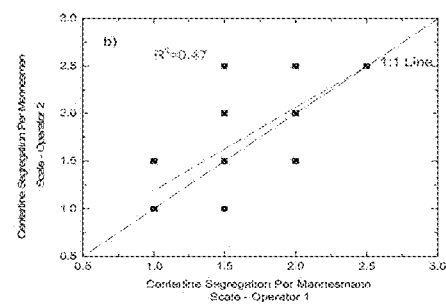
FIG. 4B is a second graph showing the results of a second set of round robin testing conducted by two operators, using conventional Mannesmann rating techniques.
Figure 6:
FIG. 6 is a series of photographs and images describing examples of portions of the Mannesmann scale images for centerline segregation from FIG. 3, before and after having been filtered and thresholded, in accordance with various embodiments of the present invention.

Prior to analyzing a particular as-cast steel product, it may be necessary to first define a continuous scale according to which such steel products may be rated. In various embodiments, this may involve defining a continuous function based on the discrete ratings of the Mannesmann scale. While various embodiments may be described as being rated according to the Mannesmann scale, or a reference curve equivalent thereof, it should be appreciated that various embodiments may be adapted for rating according to other rating scales known in the art. The continuous function based on the Mannesmann scale may be defined according to multi-step analysis of the images provided in the Mannesmann charts. For example, the images from the Mannesmann charts shown in FIG. 3 may be provided to image filter 520 to filter noise from the associated images. The images may then be provided to threshold engine 530, which thresholds the images into binary, black-and-white images so as to isolate the internal defects from the images. FIG. 6 shows examples of portions of the Mannesmann scale images for centerline segregation from FIG. 3, both before (above) and after (below) having been filtered and thresholded. As can be seen, after filtering and thresholding, the internal defects—in this case, segregates—have been substantially isolated out of the original images. In various embodiments, the images may be thresholded at a threshold level between 60% and 70%. In some of those embodiments, the threshold level may be 65%.

Once the Mannesmann charts have been filtered and thresholded, they may then be passed to internal defect area engine 540. Internal defect area engine 540 is adapted to determine the fraction (or percentage or ratio) of the images occupied by the internal defects, such as under the following formula:

$$F_D = \frac{A_D}{A_O}, \tag{1}$$

where $A_D$ is the internal defect area and $A_O$ is the overall area. It should be appreciated that for a particular type of defect, the defect is generally found in a certain area of the steel product, and thus it is generally unnecessary to analyze areas of the product where such internal defects are generally not found. Further, if too large an area is analyzed relative to the area where internal defects are expected to be found, the denominator of the fraction would be so large that even relatively large differences in the amount of internal defects would have only a minimal effect on the overall magnitude of the fraction. Accordingly, as shown in FIG. 6, in various embodiments, the "overall area" that is analyzed and calculated may be an area that is less than the total area of the surface being analyzed. In some embodiments, the overall area analyzed may be the area within which internal defects are most likely to be found. In some embodiments (such as in the case of centerline segregation), the overall area may comprise the area that is about ±0.425 inches from the centerline of the product. In other embodiments, the overall area may comprise the area that is about ±0.3 inches from the centerline of the product. In yet other embodiments, the overall area may comprise the area that is about ±0.25 inches from the centerline of the product. In yet other embodiments, the overall area may comprise a hypothetical equi-axed region of the product. In yet other embodiments, the overall area may comprise the regions between the centerline and the top or bottom surface of the as-cast product in case of mid-way (radial) cracks, mid-way (transverse) cracks, cloud-shape inclusions and spot-shaped inclusions; and between the triple point and the edge (e.g. the shorter edge) of the surface of the as-cast product in the case of narrow side cracks and corner cracks. Further, it should be appreciated that the overall area to be analyzed may be determined at any time prior to or after image filtering and/or thresholding. Once the internal defect area fractions of the Mannesmann charts have been determined, those fractions can be used to define a reference curve of internal defect area fractions versus the Mannesmann scale (FIG. 8).

Figure 8:
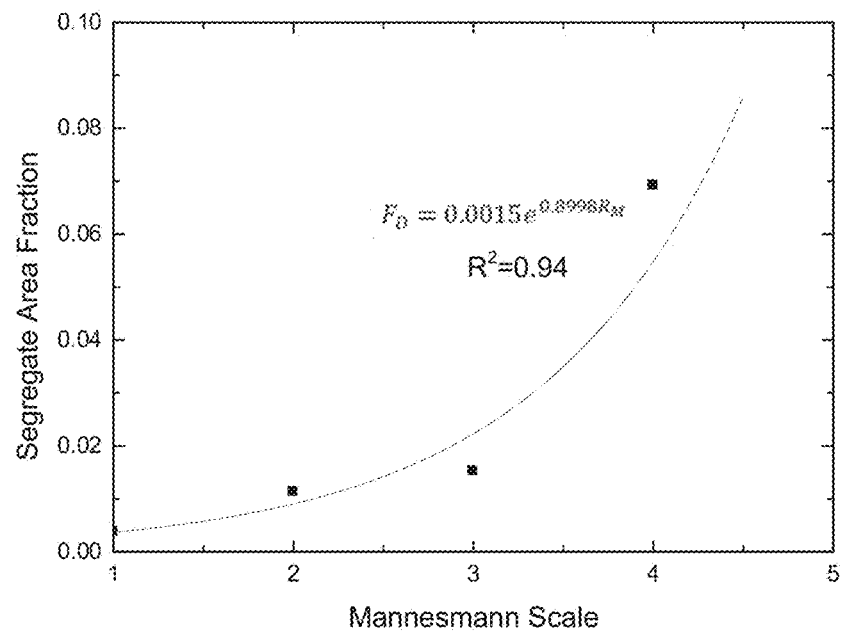
FIG. 8 illustrates a graph plotting the determined internal defect area fractions from the Mannesmann charts for centerline segregation, for ratings 1 to 4, as well as an example reference curve based on those plots, in accordance with various embodiments of the present invention.

FIG. 8 illustrates a graph plotting the determined internal defect area fractions ($F_D$) of the Mannesmann charts for centerline segregation, for ratings 1-4, versus those ratings ($R_M$), as well as an example reference curve based on those plots. Rating 5 of the Mannesmann scale was not used in the illustrated embodiment because products exhibiting that level of segregation are rarely observed, due to the quality of fabrication at most steel plants and also because a rating of 5 is given to as-cast products exhibiting a continuous crack in the mid-thickness region. As shown, the curve has a relatively high correlation coefficient of 0.94 and generally tracks the equation:

$$F_D = 0.0015 e^{0.8998 R_M} \quad (2)$$

Rearranging the above equation provides the following equation for determining the Mannesmann rating as a function of the segregate area fraction:

$$R_M = \frac{1}{0.8998} \ln\left(\frac{F_D}{0.0015}\right) \quad (3)$$

Figure 10:
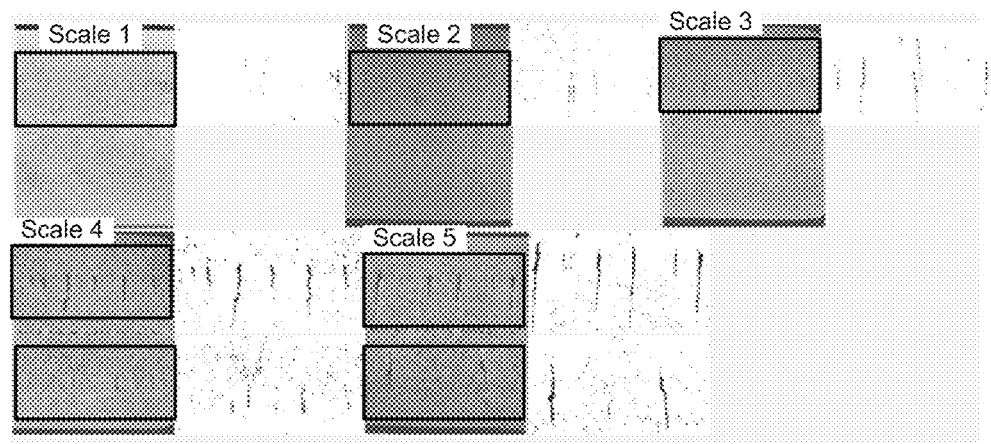
FIG. 10 is a series of photographs and corresponding images showing examples of the Mannesmann scale images for longitudinal (radial) internal cracks, before and after having been filtered and thresholded, in accordance with various embodiments of the present invention.

Similar processes may be followed in order to determine reference curves for other types of internal defects. For example, FIG. 10 shows examples of the Mannesmann scale images for longitudinal (radial) internal cracks, before (left) and after (right) having been filtered and thresholded. Based on an analysis of those images, an example reference curve for determining the Mannesmann rating based on the internal defect area fraction of longitudinal (radial) internal cracks may be formulated as follows:

$$R_M = \frac{1}{0.8544} \ln\left(\frac{F_D}{0.00001}\right) \quad (4)$$

Figure 11:
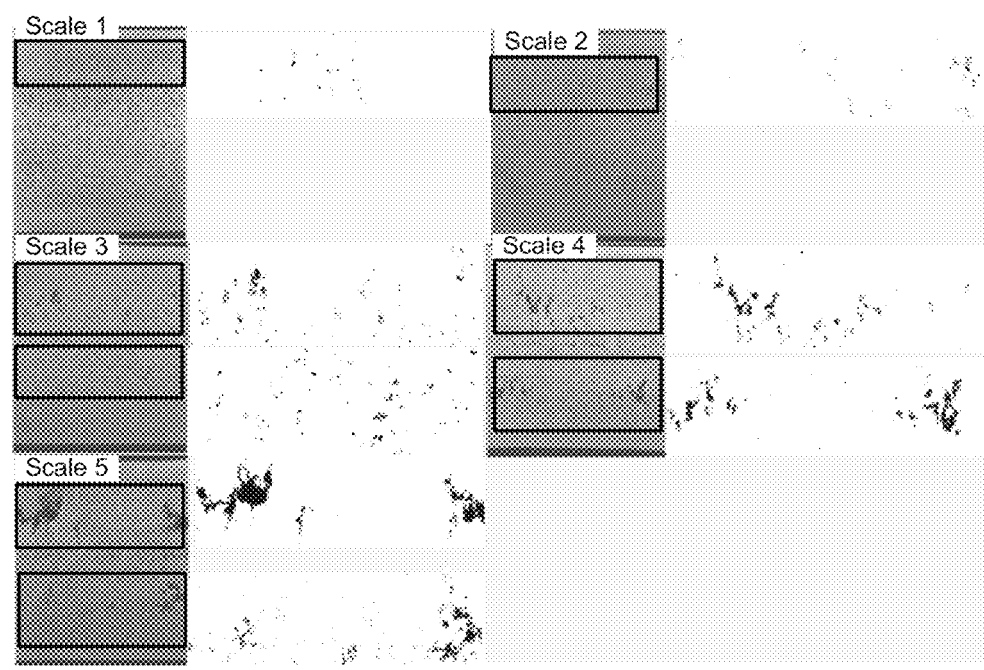
FIG. 11 is a series of photographs and corresponding images showing examples of the Mannesmann scale images for transverse (halfway) internal cracks, before and after having been filtered and thresholded, in accordance with various embodiments of the present invention.

FIG. 11 shows examples of the Mannesmann scale images for transverse (halfway) internal cracks, before (left) and after (right) having been filtered and thresholded. Based on an analysis of those images, an example reference curve for determining the Mannesmann rating based on the internal defect area fraction of transverse (halfway) internal cracks may be formulated as follows:

$$R_M = \frac{1}{1.2391} \ln\left(\frac{F_D}{0.000003}\right) \quad (5)$$

Figure 12:
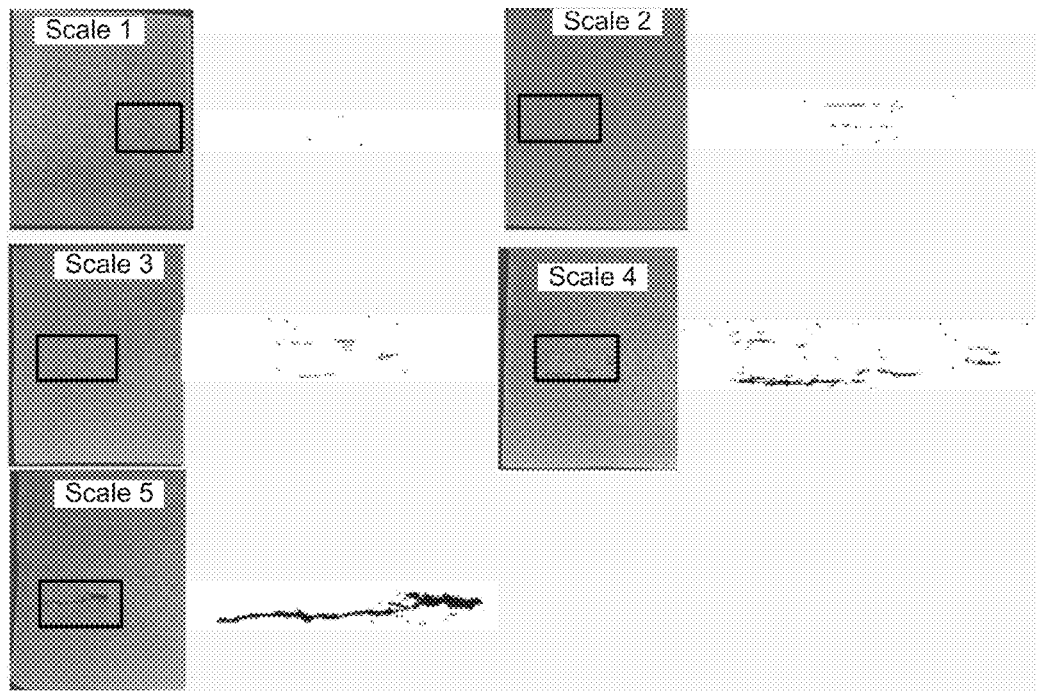
FIG. 12 is a series of photographs and corresponding images showing examples of the Mannesmann scale images for narrow side internal cracks, before and after having been filtered and thresholded, in accordance with various embodiments of the present invention.

FIG. 12 shows examples of the Mannesmann scale images for narrow side internal cracks, before (left) and after (right) having been filtered and thresholded. Based on an analysis of those images, an example reference curve for determining the Mannesmann rating based on the internal defect area fraction of narrow side internal cracks may be formulated as follows:

$$R_M = \frac{1}{1.2128} \ln\left(\frac{F_D}{0.0000008}\right) \quad (6)$$

Figure 13:
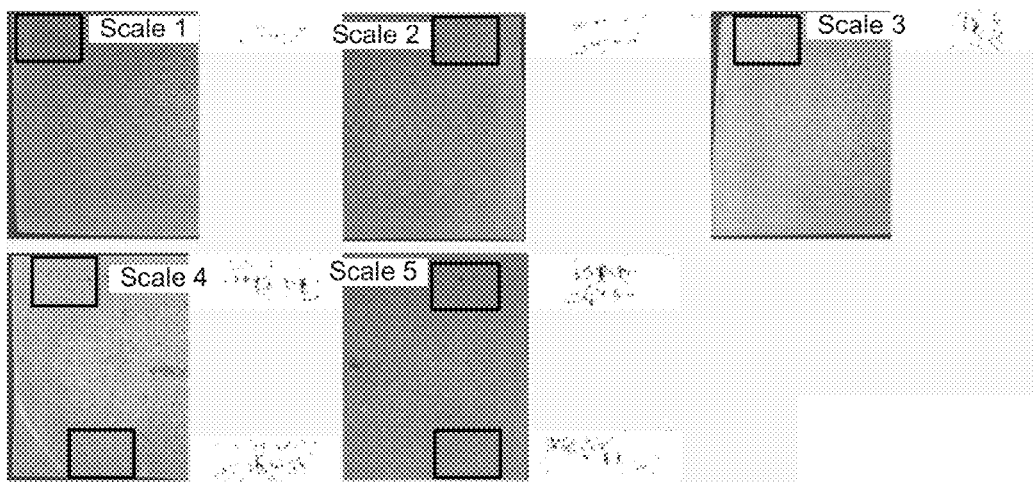
FIG. 13 is a series of photographs and corresponding images showing examples of the Mannesmann scale images for corner internal cracks, before and after having been filtered and thresholded, in accordance with various embodiments of the present invention.

FIG. 13 shows examples of the Mannesmann scale images for corner internal cracks, before (left) and after (right) having been filtered and thresholded. Based on an analysis of those images, an example reference curve for determining the Mannesmann rating based on the internal defect area fraction of corner internal cracks may be formulated as follows:

$$R_M = \frac{1}{0.6516} \ln\left(\frac{F_D}{0.00001}\right) \quad (7)$$

Figure 14:
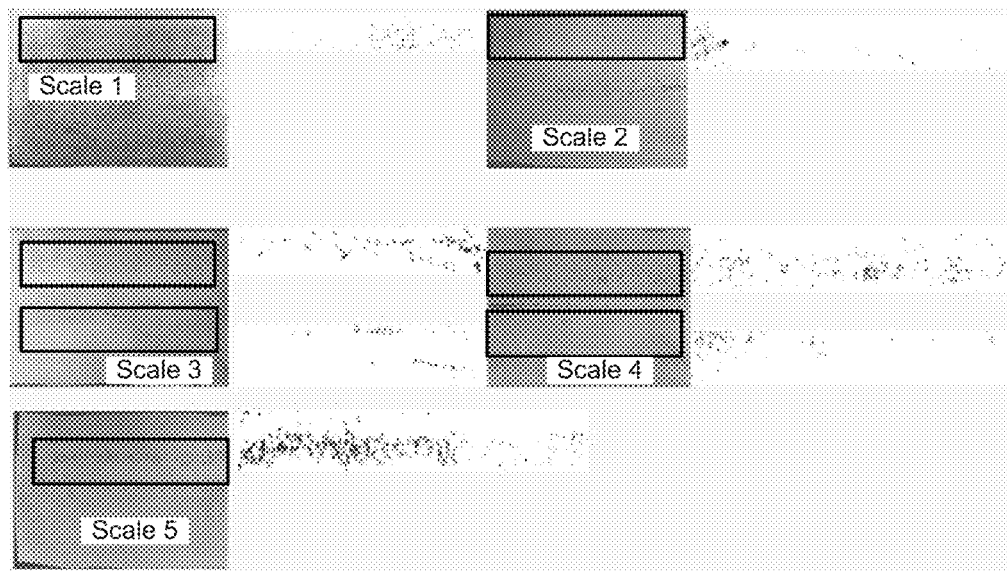
FIG. 14 is a series of photographs and corresponding images showing examples of the Mannesmann scale images for cloud-shaped inclusions, before and after having been filtered and thresholded, in accordance with various embodiments of the present invention.

FIG. 14 shows examples of the Mannesmann scale images for cloud-shaped inclusions, before (left) and after (right) having been filtered and thresholded. Based on an analysis of those images, an example reference curve for determining the Mannesmann rating based on the internal defect area fraction of cloud-shaped inclusions may be formulated as follows:

$$R_M = \frac{1}{0.6661} \ln\left(\frac{F_D}{0.00001}\right) \quad (8)$$

Figure 15:
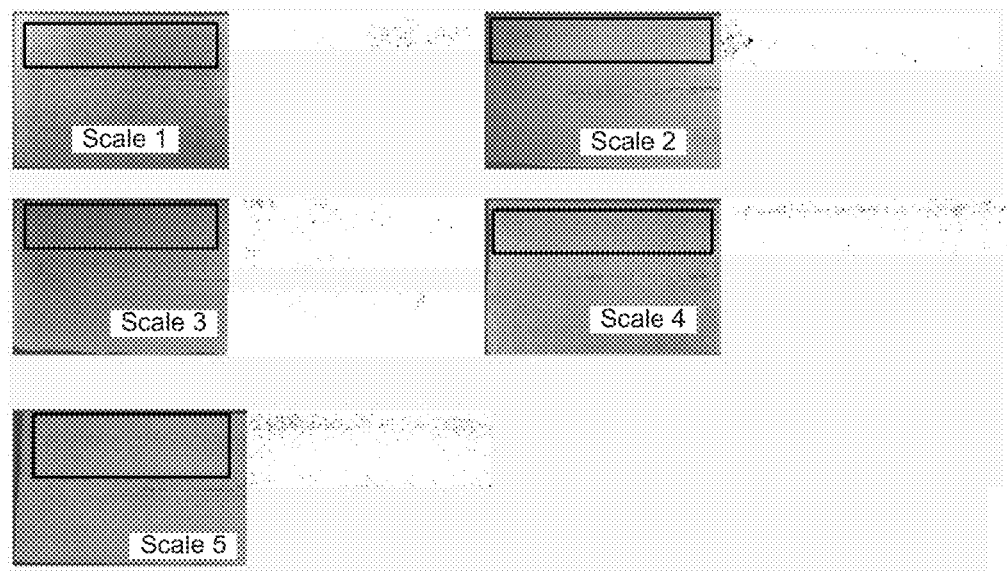
FIG. 15 is a series of photographs and corresponding images showing examples of the Mannesmann scale images for spot-shaped inclusions, before and after having been filtered and thresholded, in accordance with various embodiments of the present invention.

FIG. 15 shows examples of the Mannesmann scale images for spot-shaped inclusions, before (left) and after (right) having been filtered and thresholded. Based on an analysis of those images, an example reference curve for determining the Mannesmann rating based on the internal defect area fraction of spot-shaped inclusions may be formulated as follows:

$$R_M = \frac{1}{0.5416} \ln\left(\frac{F_D}{0.00001}\right) \quad (9)$$

As should be appreciated, Equations 3 through 9 above all generally take the form:

$$R_M = \frac{1}{a}\ln\left(\frac{F_D}{b}\right) = \frac{1}{a}\ln\left(\frac{A_D/A_O}{b}\right), \quad (10)$$

where a and b are constants that are selected based on the type of defect.

Figure 2:
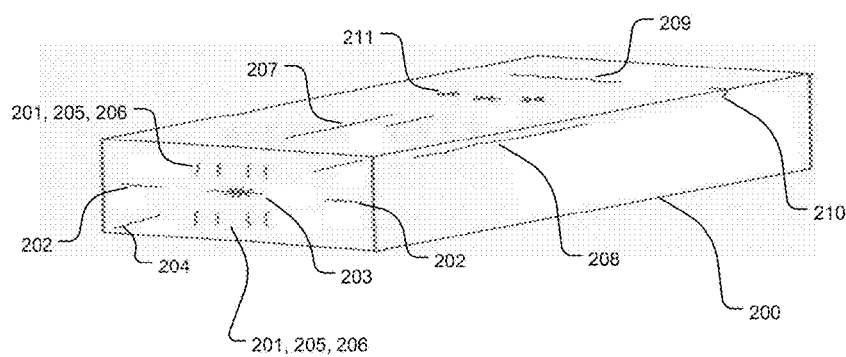
FIG. 2 is a diagram showing examples of various types of defects commonly found in an as-cast steel product.

Having established reference curves for various types of defects, as-cast steel products can be more effectively analyzed and rated for such defects, such as one or more of those shown in FIG. 2. Once an as-cast product 200 is produced from the caster, surface 250 of product 200 may be prepared for analysis. This may involve, for example, grinding surface 250 with a grinder. It may also involve etching surface 250, e.g., in an etching bath. In some embodiments, the etchant may comprise a hydrochloric acid etchant, an ammonium persulfate etchant, or the like. It should be appreciated that the etching should be performed in such a manner so as to avoid stains on the etched surface 250, or the results of the analysis may be skewed. Similarly, product 200 should be machined so as to avoid machining marks that can lead to artifacts.

Figure 7:
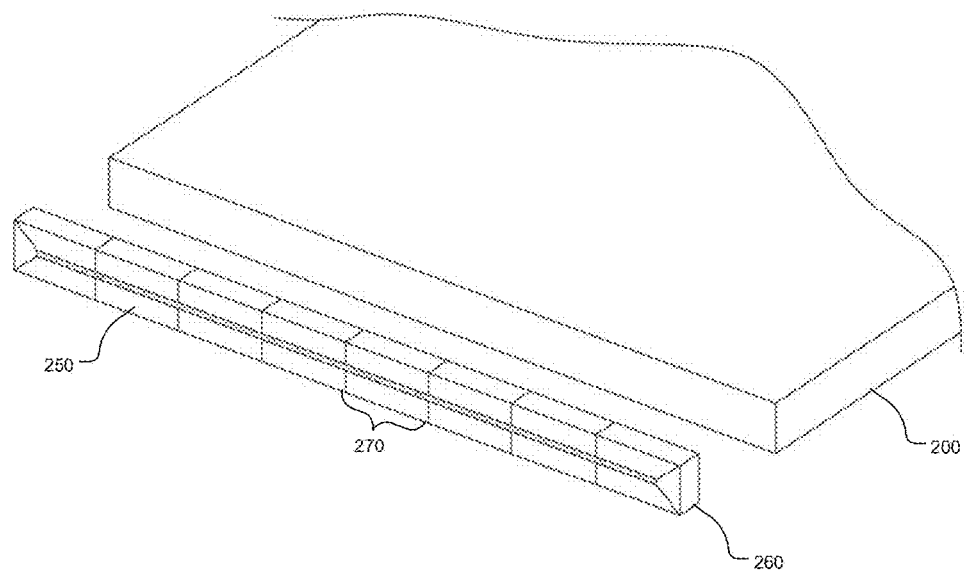
FIG. 7 is an illustration showing exemplary sample and sub-samples that may be cut from an as-cast product, in accordance with various embodiments of the present invention.

With reference again to FIG. 5, once prepared for analysis, surface 250 of as-cast product 200 may be scanned by optical scanner so as to create a digital image thereof. As shown in FIG. 7, sample 260 containing surface 250 may be cut from as-cast product 200 in some embodiments for ease of handling and analysis. Sample 260 may comprise either a transverse or longitudinal cut from product 200 with varying dimension. To further ease handling and analysis, sample 260 may be further cut into sub-samples 270.

Once surface 250 has been scanned to a digital image (or, in the case of a sample 260 divided into sub-samples 270, digital sub-images), the image may be provided to image filter 520 to filter noise therefrom. The image may then be provided to threshold engine 530, which may threshold the images into binary, black-and-white images so as to isolate the internal defects from the images—similar to the manner in which the images of the Mannesmann charts were thresholded, as shown in FIG. 6.

Once the image has been filtered and thresholded, it may then be passed to internal defect area engine 540. Internal defect area engine 540 once again is adapted to determine the fraction (or percentage or ratio) of the image occupied by the internal defects, such as the fraction of Equation 1. In the case where multiple sub-samples 270 are separately scanned, their individual internal defect area fractions may be formulated as:

$$F_{Di} = \frac{A_{Di}}{A_{Oi}}, \quad (11)$$

where $A_{Di}$ is the area of internal defects in sub-samples, and $A_{Oi}$ is the area of the region containing the defects in sub-samples.

As with the analysis of the Mannesmann charts, in various embodiments, the "overall area" that is analyzed and calculated may be some area that is less than the total area of the surface being analyzed. In some embodiments, the overall area analyzed may be the area within which internal defects are most likely to be found. In some embodiments, the overall area may comprise the area that is about ±0.425 inches from the centerline of the product. In other embodiments, the overall area may comprise the area that is about ±0.3 inches from the centerline of the product. In yet other embodiments, the overall area may comprise the area that is about ±0.25 inches from the centerline of the product. In yet other embodiments, the overall area may comprise a hypothetical equi-axed region of the product. In yet other embodiments, the overall area may comprise the regions between the centerline and the top or bottom surface of the as-cast product in case of mid-way (radial) cracks, mid-way (transverse) cracks, cloud-shape inclusions and spot-shaped inclusions; and between the triple point and the edge (e.g. the shorter edge) of the surface of the as-cast product in the case of narrow side cracks and corner cracks.

Once the internal defect area fraction (or sub-fractions) has been determined, the fraction may be passed to normalizer 550, which may calculate an equivalent Mannesmann rating for the internal defects within surface 250. This may be achieved, for example, by substituting the internal defect area fraction into the appropriate one of Equations 3 to 9 above that corresponds to the type of defect being analyzed. In some embodiments in which product 200 is cut into multiple sub-samples 270, an average internal defect area fraction ($F_{Davg}$) for centerline segregation may be formulated as follows:

$$F_{Davg} = \frac{1}{n}\sum_{i=1}^{n}\frac{A_{Di}}{A_{Oi}}, \quad (12)$$

where n is the number of sub-samples 270 cut from product 200, $A_{Di}$ is the area of internal defects in sub-samples and $A_{Oi}$ is the area of the region containing the defects in sub-samples. In some other embodiments in which product 200 is cut into multiple sub-samples 270, an total internal defect area fraction ($F_{Dtot}$) may be formulated as follows:

$$F_{Dtot} = \sum_{i=1}^{n}\frac{A_{Di}}{A_{Oi}} \quad (13)$$

The equivalent Mannesmann rating may then be determined by substituting the value of $F_{Davg}$ or $F_{Dtot}$ into the appropriate one of Equations 3 to 9. Alternatively, the sub-fractions ($F_{Di}$) corresponding to each of the sub-samples 270 may each be substituted into the appropriate one of Equations 3 to 9 to obtain corresponding sub-ratings ($R_{Mi}$), which may then be averaged. Once the Mannesmann equivalent rating has been determined, it may be passed to an output device 560, such as a monitor, printer, transmission line (e.g., for communication to another person or device), or storage device (e.g., for storage within a data file). $F_{Davg}$ values may range from 1 to 4.9 and $F_{Dtot}$ values range from 0 to 4.

Figure 9:
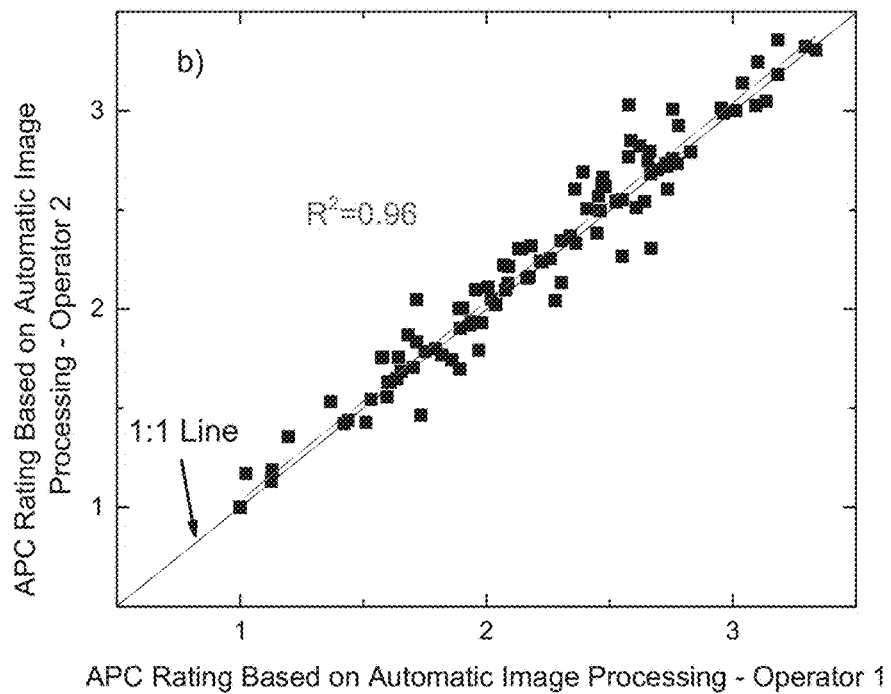
FIG. 9 is a graph plotting the results of a round robin test conducted by two operators using the systems and processes of an embodiment of the present invention.

Thus, various embodiments provide automated and objective systems and processes for quantifying internal defects in as-cast steel products in a highly granular manner. By calculating internal defect area fraction and then fitting the fraction to a continuous reference curve that represents a known, discrete rating system, various embodiments are able to remove the subjectivity—and thus high degree of variation—from the quantification of internal defects. For example, FIG. 9 shows the results of a round-robin test conducted by two operators using the systems and processes of an embodiment of the present invention. As shown, with very limited exception, the results achieved by both operators were highly consistent, exhibiting a correlation coefficient of 0.96. The variation that remains between the two operators can be attributed to slight differences in the portions of the product surfaces (i.e., the hypothetical equiaxed regions) that each operator chose to analyze. As noted above, the size of the area to be analyzed can be standardized and automated, which can drive the correlation coefficient to, or very close to, 1.

The use of one or more of the disclosed rating systems for assessment of the severity of internal defects also offers a potential for process optimization. For example, the assessed quality can be used to optimize various production parameters, such as soft reduction window, cast speed, or the like. Further, if analysis shows that defects are frequently occurring at generally the same location of a product, then certain components of the caster can be adjusted or repaired accordingly. The chemistry of the product can be also optimized to ensure a good internal quality is achieved in the product.

Figure 16:
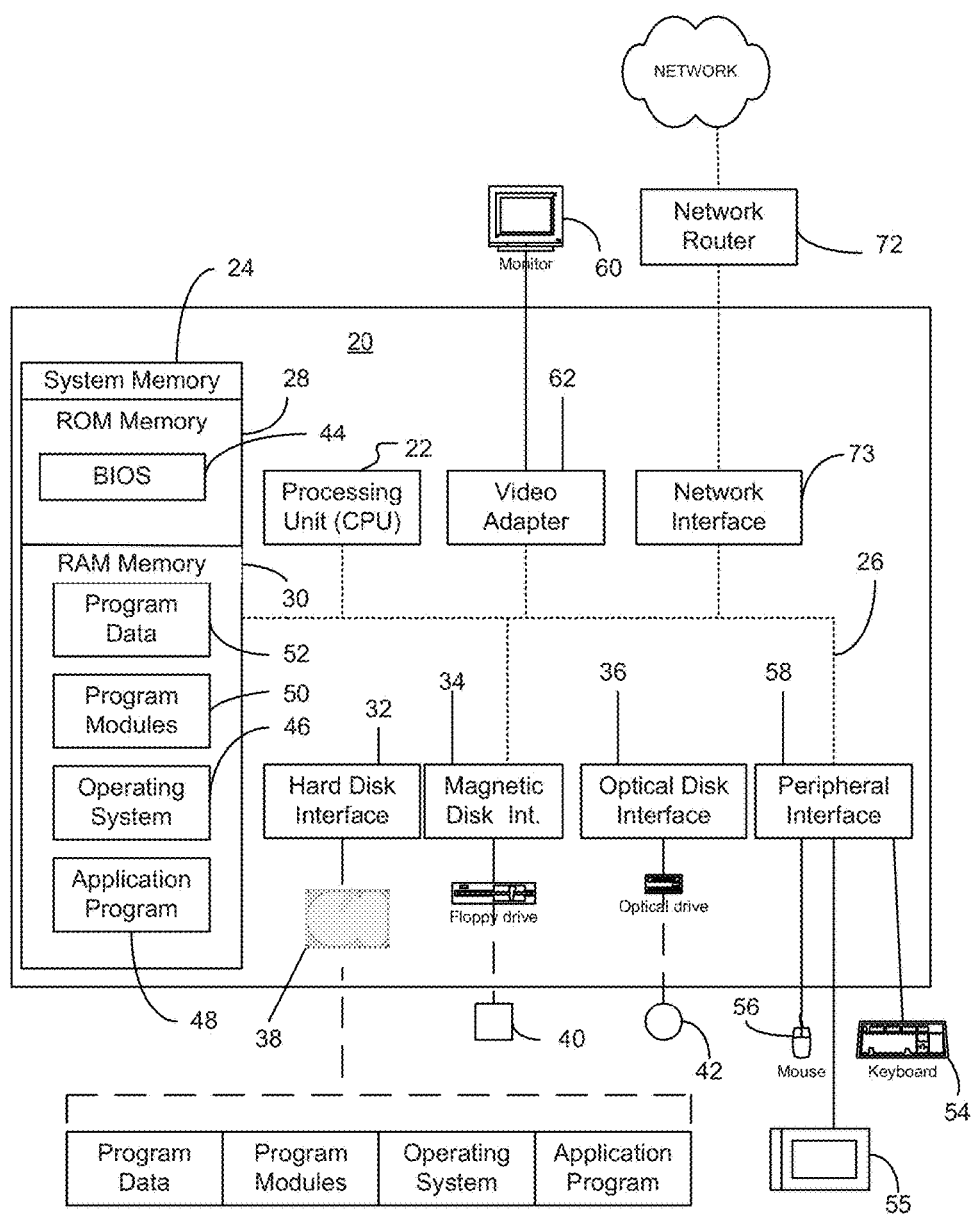
FIG. 16 is a block diagram of an exemplary computing system environment within which various aspect of embodiments may be implemented.

Certain portions of various embodiments may be implemented in a computing system environment. FIG. 16 illustrates an exemplary computing system environment 20, such as a desktop computer, laptop, smartphone, tablet, or any other such device having the ability to execute instructions, such as those stored within a non-transient, computer-readable medium. Furthermore, while described and illustrated in the context of a single computing system 20, those skilled in the art will also appreciate that the various tasks described hereinafter may be practiced in a distributed environment having multiple computing systems 20 linked via a local or wide-area network, in which the executable instructions may be associated with and/or executed by one or more of multiple computing systems 20.

In its most basic configuration, computing system environment 20 typically includes at least one processing unit 22 and at least one memory 24, which may be linked via a bus 26. Depending on the exact configuration and type of computing system environment, memory 24 may be volatile (such as RAM 30), non-volatile (such as ROM 28, flash memory, etc.) or some combination of the two. Computing system environment 20 may have additional features and/or functionality. For example, computing system environment 20 may also include additional storage (removable and/or non-removable) including, but not limited to, magnetic or optical disks, tape drives and/or flash drives. Such additional memory devices may be made accessible to the computing system environment 20 by means of, for example, a hard disk drive interface 32, a magnetic disk drive interface 34, and/or an optical disk drive interface 36. As will be understood, these devices, which would be linked to the system bus 26, respectively, allow for reading from and writing to a hard disk 38, reading from or writing to a removable magnetic disk 40, and/or for reading from or writing to a removable optical disk 42, such as a CD/DVD ROM or other optical media. The drive interfaces and their associated computer-readable media allow for the nonvolatile storage of computer readable instructions, data structures, program modules and other data for computing system environment 20. Those skilled in the art will further appreciate that other types of computer readable media that can store data may be used for this same purpose. Examples of such media devices include, but are not limited to, magnetic cassettes, flash memory cards, digital videodisks, Bernoulli cartridges, random access memories, nano-drives, memory sticks, other read/write and/or read-only memories and/or any other method or technology for storage of information such as computer readable instructions, data structures, program modules or other data. Any such computer storage media may be part of computing system environment 20.

A number of program modules may be stored in one or more of the memory/media devices. For example, a basic input/output system (BIOS) 44, containing the basic routines that help to transfer information between elements within computing system environment 20, such as during start-up, may be stored in ROM 28. Similarly, RAM 30, hard drive 38, and/or peripheral memory devices may be used to store computer executable instructions comprising operating system 46, one or more applications programs 48, other program modules 50, and/or program data 52. Still further, computer-executable instructions may be downloaded to one or more of the computing devices as needed, for example, via a network connection.

An end-user, e.g. a consumer, may enter commands and information into the computing system environment 20 through input devices such as keyboard 54 and/or pointing device 56. Further, information may be received from other peripheral input devices, such as scanner 55, which in various embodiments may be optical scanner 510. While not illustrated, other input devices may include a microphone, a joystick, a game pad, a scanner, etc. These and other input devices would typically be connected to processing unit 22 by means of peripheral interface 58 which, in turn, would be coupled to bus 26. Input devices may be directly or indirectly connected to processor 22 via interfaces such as, for example, a parallel port, game port, firewire, or a universal serial bus (USB). To view information from the computing system environment 20, monitor 60 or another type of display device may also be connected to bus 26 via an interface, such as via video adapter 62. In addition to monitor 60, computing system environment 20 may also include other peripheral output devices, not shown, such as speakers and printers.

Computing system environment 20 may also utilize logical connections to one or more computing system environments. In this regard, it will be appreciated that the remote computing system environment may, like computing system environment 20, be any type of device having processing capabilities. Again, it will be appreciated that the remote computing system environment need not be implemented as a single device but may be implemented in a manner such that the tasks performed by the remote computing system environment are distributed to a plurality of computing system environments linked through a communication network.

For performing tasks as needed, the remote computing system environment may include many or all of the elements described above relative to computing system environment 20. Communications between computing system environment 20 and the remote computing system environment may be exchanged via a further processing device, such as network router 72, that is responsible for network routing. Communications with network router 72 may be performed via network interface component 73. Thus, within such a networked environment, e.g., the Internet, World Wide Web, LAN, or other like type of wired or wireless network, it will be appreciated that program modules depicted relative to computing system environment 20, or portions thereof, may be stored in the memory storage device(s) of the remote computing system environment.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method for quantitatively measuring internal defects in an as-cast steel product, comprising:
   optically scanning at least a portion of a surface of the steel product with a scanning device to create a digital image thereof;
   thresholding the image in a thresholding engine to isolate internal defects within the image;
   analyzing the thresholded image to determine an internal defect area, wherein the internal defect area comprises an area of at least a portion of the thresholded image that is occupied by the internal defects;
   determining an overall area of the portion of the thresholded image;
   calculating a fraction of the internal defect area relative to the overall area; and
   calculating an equivalent Mannesmann scale rating of the internal defects in the steel product based on the fraction.

2. The method as recited in claim 1, further comprising:
   etching the surface of the steel product prior to optically scanning the portion of the surface.

3. The method as recited in claim 2, wherein etching the surface of the steel product comprises etching the surface with a hydrochloric acid etchant.

4. The method as recited in claim 2, wherein etching the surface of the steel product comprises etching the surface with an ammonium persulfate etchant.

5. The method as recited in claim 2, further comprising:
   grinding the surface of the steel product prior to etching the surface.

6. The method as recited in claim 2, further comprising:
   cutting a sample from the steel product prior to etching the surface, the sample including the surface.

7. The method as recited in claim 6, wherein cutting the sample from the steel product comprises cutting a transverse section from the steel product.

8. The method as recited in claim 6, wherein cutting the sample from the steel product comprises cutting a longitudinal section from the steel product.

9. The method as recited in claim 6, further comprising:
   cutting the sample into a plurality of sub-samples, the sub-samples comprising sub-surfaces of the surface.

10. The method as recited in claim 9,
    wherein optically scanning at least a portion of the surface of the steel product comprises optically scanning at least portions of the sub-surfaces of the sub-samples to create a plurality of corresponding digital sub-images,
    wherein thresholding the image in the thresholding engine to isolate internal defects within the image comprises thresholding the sub-images in the thresholding engine to isolate internal defects within the sub-images,
    wherein analyzing the thresholded image to determine the internal defect area comprises analyzing the thresholded sub-images to determine corresponding internal defect sub-areas, wherein the internal defect sub-areas comprise areas of at least portions of the corresponding thresholded sub-images that are occupied by the internal defects,
    wherein determining the overall area of the portion of the thresholded image comprises determining overall sub-areas of the portions of the thresholded sub-images,
    wherein calculating the fraction of the internal defect area relative to the overall area comprises calculating sub-fractions of the internal defect sub-areas to the corresponding overall sub-areas, and
    wherein calculating the equivalent Mannesmann scale rating based on the fraction comprises calculating equivalent Mannesmann scale sub-ratings based on each of the sub-fractions.

11. The method as recited in claim 10, wherein the equivalent Mannesmann scale rating comprises an average of the sub-ratings.

12. The method as recited in claim 11, further comprising:
    determining a highest sub-rating from the calculated sub-ratings.

13. The method as recited in claim 1, wherein the scanning device comprises a portable scanner.

14. The method as recited in claim 1, wherein the scanning device comprises a flatbed scanner.

15. The method as recited in claim 1, wherein the scanning device comprises non-contact scanner.

16. The method as recited in claim 1, wherein thresholding the image in the thresholding engine to isolate internal defects within the image comprises thresholding the image at a threshold level of between 60% and 70%.

17. The method as recited in claim 1, wherein thresholding the image in the thresholding engine to isolate internal defects within the image comprises thresholding the image at a threshold level of 65%.

18. The method as recited in claim 1, wherein the portion of the thresholded image that is analyzed corresponds to the region where internal defects are most commonly found in other steel products of the same type as the steel product.

19. The method as recited in claim 18, wherein the portion of the thresholded image that is analyzed comprises a region extending about 0.425 inches from a centerline of the steel product.

20. The method as recited in claim 18, wherein the portion of the thresholded image that is analyzed comprises a region extending about 0.3 inches from a centerline of the steel product.

21. The method as recited in claim 18, wherein the portion of the thresholded image that is analyzed comprises a region extending about 0.25 inches from a centerline of the steel product.

22. The method as recited in claim 1, wherein the portion of the thresholded image that is analyzed corresponds to an equi-axed region of the surface.

23. The method as recited in claim 1, wherein the portion of the thresholded image that is analyzed corresponds to a region between a centerline of the product and an edge of the surface.

24. The method as recited in claim 1, wherein the portion of the thresholded image that is analyzed corresponds to a region between a triple point of the surface and an edge of the surface.

25. The method as recited in claim 1, wherein calculating the equivalent Mannesmann scale rating based on the fraction comprises:
    determining where the fraction falls on a curve representing the relationship between Mannesmann scale ratings versus internal defect area fraction.

26. The method as recited in claim 25, wherein the curve is represented by the equation:

$$R_M = \frac{1}{a} \ln\left(\frac{A_D/A_O}{b}\right)$$

wherein $R_M$ is the equivalent Mannesmann scale rating, "a" and "b" are constants that are based on the type of the internal defect, $A_D$ is the internal defect area and $A_O$ is the overall area.

27. The method as recited in claim 1, wherein the as-cast steel product comprises a slab.

28. The method as recited in claim 1, wherein the as-cast steel product comprises a billet.

29. The method as recited in claim 1, wherein the as-cast steel product comprises a bloom.

30. The method as recited in claim 1, wherein the as-cast product comprises a beam blank.

31. The method as recited in claim 1, further comprising: filtering the image prior to thresholding the image.

32. A system for quantitatively measuring internal defects in an as-cast steel product, comprising:
an optical scanner adapted to scan at least a portion of a surface of the steel product to create a digital image thereof;
a threshold engine communicatively coupled with the optical scanner and adapted to threshold the image to isolate internal defects within the image;
a internal defect area engine communicatively coupled with the threshold engine and adapted to:
receive the thresholded image from the threshold engine;
analyze the thresholded image to determine an internal defect area, wherein the internal defect area comprises an area of at least a portion of the thresholded image that is occupied by the internal defects;
determine an overall area of the portion of the thresholded image; and
calculate a fraction of the internal defect area relative to the overall area; and
a normalizer communicatively coupled with the internal defect area engine and adapted to:
receive the fraction of the internal defect area relative to the overall area from the internal defect area engine; and
calculate an equivalent Mannesmann scale rating of the internal defects in the steel product based on the fraction.

33. The system as recited in claim 32, further comprising: an etching bath comprising an etchant for etching the surface of the steel product.

34. The system as recited in claim 33, wherein the etchant comprises a hydrochloric acid etchant.

35. The system as recited in claim 33, wherein the etchant comprises an ammonium persulfate etchant.

36. The system as recited in claim 33, further comprising: a grinder for grinding the surface of the steel product prior to etching the surface.

37. The system as recited in claim 33, wherein the surface is located on a sample cut from the steel product prior to the surface being etched.

38. The system as recited in claim 33, wherein the sample comprises a transverse section cut from the steel product.

39. The system as recited in claim 33, wherein the sample comprises a longitudinal section cut from the steel product.

40. The system as recited in claim 33, wherein the sample is cut into a plurality of sub-samples, the sub-samples comprising sub-surfaces of the surface.

41. The system as recited in claim 40,
wherein the optical scanner scans at least a portion of the surface of the steel product by optically scanning at least portions of the sub-surfaces of the sub-samples to create a plurality of corresponding digital sub-images,
wherein the threshold engine thresholds the image to isolate internal defects within the image by thresholding the sub-images to isolate internal defects within the sub-images,
wherein the internal defect area engine analyzes the thresholded image to determine the internal defect area by analyzing the thresholded sub-images to determine corresponding internal defect sub-areas, wherein the internal defect sub-areas comprise areas of at least portions of the corresponding thresholded sub-images that are occupied by the internal defects,
wherein the internal defect area engine determines the overall area of the portion of the thresholded image by determining overall sub-areas of the portions of the thresholded sub-images,
wherein the internal defect area engine calculates the fraction of the internal defect area relative to the overall area by calculating sub-fractions of the internal defect sub-areas to the corresponding overall sub-areas, and
wherein the normalizer calculates the equivalent Mannesmann scale rating based on the fraction by calculating equivalent Mannesmann scale sub-ratings based on each of the sub-fractions.

42. The system as recited in claim 41, wherein the equivalent Mannesmann scale rating comprises an average of the sub-ratings.

43. The system as recited in claim 42, wherein the normalizer is adapted to determine a highest sub-rating from the calculated sub-ratings.

44. The system as recited in claim 32, wherein the optical scanner comprises a portable scanner.

45. The system as recited in claim 32, wherein the optical scanner comprises a flatbed scanner.

46. The system as recited in claim 32, wherein the optical scanner comprises a non-contact scanner.

47. The system as recited in claim 32, wherein the thresholding engine is adapted to threshold the image at a threshold level of between 60% and 70%.

48. The system as recited in claim 32, wherein the thresholding engine is adapted to threshold the image at a threshold level of 65%.

49. The system as recited in claim 32, wherein the portion of the thresholded image that is analyzed corresponds to the region where internal defects are most commonly found in other steel products of the same type as the steel product.

50. The system as recited in claim 49, wherein the portion of the thresholded image that is analyzed comprises a region extending about 0.425 inches from a centerline of the steel product.

51. The system as recited in claim 49, wherein the portion of the thresholded image that is analyzed comprises a region extending about 0.3 inches from a centerline of the steel product.

52. The system as recited in claim 49, wherein the portion of the thresholded image that is analyzed comprises a region extending about 0.25 inches from a centerline of the steel product.

53. The method as recited in claim 32, wherein the portion of the thresholded image that is analyzed corresponds to an equi-axed region of the surface.

54. The method as recited in claim 32, wherein the portion of the thresholded image that is analyzed corresponds to the area of the region between the centerline and the surface (top or bottom) of the as-cast products.

55. The method as recited in claim 32, wherein the portion of the thresholded mage that is analyzed corresponds to the area of the region between the triple point and an edge of the surface.

56. The system as recited in claim 32, wherein the normalizer is adapted to calculate the equivalent Mannesmann scale rating based on the fraction by determining where the fraction falls on a curve representing the relationship between the Mannesmann scale and internal defect area fraction.

57. The system as recited in claim 56, wherein the curve is represented by the equation:

$$R_M = \frac{1}{a}\ln\left(\frac{A_D/A_O}{b}\right)$$

wherein $R_M$ is the equivalent Mannesmann scale rating, "a" and "b" are constants that are based on the type of the internal defect, $A_D$ is the internal defect area and $A_O$ is the overall area.

58. The system as recited in claim 32, wherein the as-cast steel product comprises a slab.

59. The system as recited in claim 32, wherein the as-cast steel product comprises a billet.

60. The system as recited in claim 32, wherein the as-cast steel product comprises a bloom.

61. The system as recited in claim 32, wherein the as-cast steel product comprises a beam blank.

62. The system as recited in claim 32, further comprising:
an image filter communicatively coupled with the optical scanner and the threshold engine and adapted to filter the image prior to the threshold engine thresholding the image.

63. A method for quantitatively measuring internal defects in an as-cast steel product, comprising:
etching a surface of the steel product with an etchant selected from the group consisting of a hydrochloric acid etchant and an ammonium persulfate etchant;
optically scanning at least a portion of the surface of the steel product with a scanning device to create a digital image thereof;
thresholding the image in a thresholding engine to isolate internal defects within the image;
analyzing the thresholded image to determine an internal defect area, wherein the internal defect area comprises an area occupied by internal defects within a predefined region of the surface;
calculating an area of the predefined region;
calculating a fraction of the internal defect area relative to the area of the predefined region; and
determining where the calculated fraction falls on a curve representing the relationship between the Mannesmann scale and internal defect area fraction; and
calculating an equivalent Mannesmann scale rating of the internal defects in the steel product based on where the fraction falls on the curve.

* * * * *